United States Patent [19]

Takaku et al.

[11] 4,221,814
[45] Sep. 9, 1980

[54] TEREPHTHALIC ACID MONOAMIDE DERIVATIVES, PROCESS FOR PREPARING THE SAME, AND AN ANTI-ALLERGIC AGENT PREPARED FROM THE SAME

[75] Inventors: Sakae Takaku, Ageo; Takashi Mori; Yasushi Murakami, both of Tokyo; Yoshiyuki Ohsugi, Izumi; Shigeyuki Kataoka, Sakado; Yasuhisa Takeda, Yokohama; Takashi Matsuno, Omiya; Yoshimitsu Iida, Wako; Akiko Ariga, Nagareyama; Akira Okazaki, Oyama; Kazuo Igusa, Tokorozawa; Toshichika Ogasawara; Minoru Shindo, both of Tokyo, all of Japan

[73] Assignee: Chugai Seiyaku Kabushiki Kaisha, Tokyo, Japan

[21] Appl. No.: 44,687

[22] Filed: Jun. 1, 1979

[30] Foreign Application Priority Data

Jun. 9, 1978 [JP] Japan .................... 53-68931
Dec. 5, 1978 [JP] Japan .................... 53-149696

[51] Int. Cl.² .................. A61K 31/245; C07C 101/44
[52] U.S. Cl. .................... 424/310; 424/319; 560/48; 562/457; 544/92
[58] Field of Search .................... 560/48; 562/457; 424/310, 319

[56] References Cited

U.S. PATENT DOCUMENTS

| | | | |
|---|---|---|---|
| 3,658,892 | 4/1972 | Martin et al. | 562/457 |
| 3,953,496 | 4/1976 | Mori et al. | 560/45 |
| 4,089,974 | 5/1978 | Conrow et al. | 562/457 |
| 4,120,895 | 10/1978 | Conrow et al. | 562/457 |
| 4,123,455 | 10/1978 | Conrow et al. | 560/48 |

*Primary Examiner*—G. T. Breitenstein
*Attorney, Agent, or Firm*—Browdy and Neimark

[57] ABSTRACT

A terephthalic acid monoamide derivative of the formula:

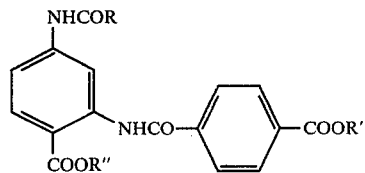

(wherein R is a straight- or branched-chain lower alkyl group; R' and R" may be the same or different, and represent a hydrogen atom, or a straight- or branched-chain lower alkyl group) or pharmaceutically acceptable salts thereof are disclosed. A process for preparing such terephthalic acid monoamide derivative or its salts, as well as an anti-allergic agent containing such derivative or its salts as an effective ingredient are also disclosed.

18 Claims, No Drawings

TEREPHTHALIC ACID MONOAMIDE DERIVATIVES, PROCESS FOR PREPARING THE SAME, AND AN ANTI-ALLERGIC AGENT PREPARED FROM THE SAME

This invention relates to a novel compound of the formula (I):

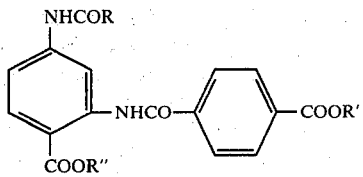
(I)

(wherein R is a straight- or branched-chain lower alkyl group; R' and R" may be the same or different, and each represents a hydrogen atom, or a straight- or branched-chain lower alkyl group) and a process for preparing such compound. It also relates to an anti-allergic agent containing such compound as an effective ingredient. The compound of the formula (I) is useful as an agent to prevent or cure allergic bronchial asthma, allergic dermatitis and other allergic diseases.

In the course of a number of bisamides derived from 2,4-diaminobenzoic acid, the inventors of this invention have successfully created some anti-allergic substances useful as medicines and have filed several patent applications on such substances. As a result of further studies, the present inventors have found that a compound of the formula (I) above wherein the amino group at 2-position of 2,4-diaminobenzoic acid is acylated with terephthalic acid or its monoalkyl ester, and the amino group at 4-position is converted to a lower aliphatic acid amide has an anti-allergic activity significantly higher than that of the compounds which the inventors have found already and that such compounds are capable of inhibiting various allergic reactions involving different species of animals and types of antibodies.

A more interesting finding is that analogous derivatives in which the amino group at 2-position of 2,4-diaminobenzoic acid is acylated phthalic acid or isophthalic acid have only weak anti-allergic activities.

The novel compound of the formula (I) according to this invention is synthesized by either of the following two methods;

(1) A compound of the formula (II):

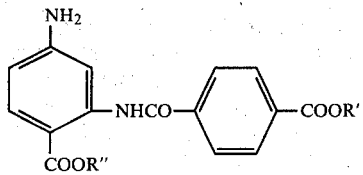
(II)

(wherein R' and R" are the same as defined above) is condensed with a reactive derivative at the carboxyl group of a compound of the formula (III):

RCOOH (III)

(wherein R is the same as defined above): or
(2) A benzoxazine derivative of the formula (IV):

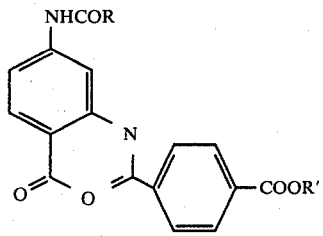
(IV)

(wherein R and R' are the same as defined above) is reacted with an alcohol or water of the formula (V):

R"—OH (V)

(wherein R" is the same as defined above).

The compound (II) to be used in this invention is readily prepared by condensing 4-nitroanthranilic acid or an ester thereof with a terephthalic acid derivative, optionally followed by hydrolysis of the condensate, and reducing the nitro group by a conventional method. The compound (IV) is readily prepared by reducing the corresponding nitro compound to produce a compound of the formula (VI):

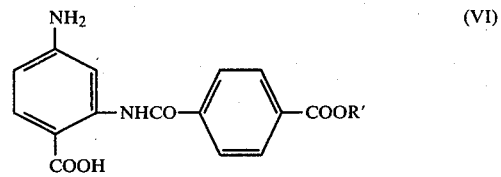
(VI)

(wherein R' is the same as defined above) and reacting said compound with a compound of the formula (VII):

RCOCl (VII)

(wherein R is the same as defined above) in pyridine.

Examples of the suitable reactive derivative at the carboxyl group of the compound (III) are an acid halide; acid anhydride; and mixed anhydrides with carbonic acid, sulfuric acid, phosphoric acid, sulfonic acid and the like. Examples of the suitable alcohols of the formula (V) are lower aliphatic alcohols such as methanol, ethanol, propanol, isopropanol, butanol, isobutanol, sec-butanol and pentanol.

The method (1) of preparing the compound (I) according to this invention is performed under conditions conventionally used for formation of an amide. To be more specific, a compound of the formula (II) is reacted with from an equivalent to 8-fold equivalent, preferably from a 1.2- to 3-fold equivalent, of a reactive derivative of a compound of the formula (III) at a temperature ranging from −10 to 100° C., preferably from 0° to 70° C. in the presence of a suitable solvent. Examples of the suitable solvent are water, benzene, toluene, tetrahydrofuran, ether, dioxane, dimethylformamide, chloroform, methylene chloride, pyridine and acetonitrile, which may be used independently or as a mixture. A condensing aid is optionally used in the method (1), and its examples include a hydroxide of an alkali metal or alkaline earth metal, an inorganic base such as carbonate or acetate, or an organic base such as pyridine or triethylamine.

The method (2) of preparing the compound (I) according to this invention is performed by heating the reaction system at a temperature of 50° to 100° C. preferably from 80° to 100° C., for a period of one to 50 hours, preferably from 2 to 10 hours, using a large excess of alcohol or water so that it also serves as a solvent or using an independent inert solvent such as tetrahydrofuran, dioxane pyridine or dimethylformamide. Better results can be obtained by performing the reaction in the presence of an equimolar to 4-fold molar amount of a reaction accelerator such as triethylamine, tributylamine, N-methyl morpholine or other tertiary amine.

The compound (I) of this invention is considered as an effective anti-allergic agent because, whether administered to animals orally or intravenously, it requires only a small dose to inhibit passive cutaneous anaphylaxis which is used as a traditional indicator for the anti-allergic effect of a substance.

The compound (I) of this invention can be administered in any desired dosage forms. To be more specific, tablet, powder, capsule or liquid is prepared by using a conventional method to incorporate the compound (I) in an excipient, binder, solvent or other vehicles generally acceptable for pharmaceutical use, such as lactose, starch, crystalline cellulose, talc, calcium carbonate, magnesium stearate, mannitol, sorbitol, benzyl alcohol and water.

The dosage and mode of administration of the compound (I) of this invention depend on the state of the patient, severity of the disease and other factors, and the dosage generally ranges from 10 to 2000 mg/day, preferably from 100 to 1000 mg/day.

For oral administration in the form of a tablet, from 50 to 200 mg of the compound (I) mixed with a suitable vehicle is compressed into a tablet, and one or two of such tablets are administered once to several times daily. Other administration forms may likewise be prepared by a conventional method, and administered in a suitable dose.

It is to be understood that an inhalant which permits topical administration has the advantage that a dosage of 1 to 200 mg/day is effective for exhibiting antiallergic effect.

Experiment

Rat antibodies to egg albumin were prepared by homologous sensitization in accordance with the following method described in Immunology, Vol. 7, page 681 (1964).

One milligram of egg albumin and $10^{10}$ cells of *Haemophilus pertussis* were injected into rats intramuscularly and intraperitoneally, respectively, and, 14 days after the injection, serum was recovered. A tenth of a milliliter of a 16-fold dilution of the serum was injected into the dorsal skin of the rats. Forty-eight hours later, each rat was intraveneously injected with 0.5 ml/100 g of a mixture containing equal volumes of a 1% solution of Evans Blue in physiological saline and 1% solution of egg albumin in physiological saline. Thirty minutes later, each rat was beheaded and phlebotomized before it was stripped of the skin and the dye which leaked from the site of serum injection was quantitatively measured; with a pair of scissors, the area stained in blue was cut into pieces which were immersed overnight in 5 ml of a mixture comprising 3 parts of a 0.5 aqueous solution of sodium sulfate and 7 parts of acetone, centrifuged at 3,000 rpm for a period of 10 minutes, and the supernatent was subjected to measurement of absorbance at 610 m$\mu$. The compound (I) of this invention was dissolved in a physiological saline in the presence of potassium carbonate to make solution (pH: 7.5 to 8.5) and either administered intravenously to the rat tail immediately before injection of Evans Blue and egg albumin, or orally administered in the form of a suspension in an aqueous solution of gum arabic 30 minutes before injection of Evans Blue and egg albumin. The percent inhibition was calculated by comparing the absorbance of Evans Blue leaking from groups of rats administered with the compound of the formula (I) with the absorbance of the dye leaking from control groups. Five rats comprised one group for which the average inhibition efficiency was calculated. The results are shown in Tables 1 and 2. In Tables 1 and 2, the rating ++++ represents an inhibition efficiency of 90% or more; +++ an inhibition efficiency of 70 to 90%; ++ an inhibition efficiency of 50 to 70%;+ an inhibition efficiency of 30 to 50%, and ±an inhibition efficiency of 0 to 30%.

Table 1

| Inhibition Efficiency by Intravenous Administration | | |
|---|---|---|
| Compounds | Dose (mg/kg) | Inhibition efficiency |
| Compound of Example 1 | 1 | ++++ |
| Compound of Example 1 | 0.1 | ++ |
| Compound of Example 2 | 2 | ++++ |
| Compound of Example 3 | 2 | ++++ |
| Compound of Example 4 | 1 | +++ |
| Compound of Example 5 | 1 | +++ |
| Compound of Example 6 | 1 | +++ |
| Compound of Example 7 | 1 | ++++ |
| Compound of Example 7 | 0.5 | ++++ |
| Compound of Example 8 | 1 | +++ |
| Compound of Example 11 | 1 | +++ |
| Compound of Example 12 | 1 | ++++ |

Table 2

| Inhibition Efficiency by Oral Administration | | |
|---|---|---|
| Compounds | Dose (mg/kg) | Inhibition efficiency |
| Compound of Example 1 | 100 | ++++ |
| Compound of Example 1 | 25 | ++ |
| Compound of Example 2 | 100 | ++++ |
| Compound of Example 3 | 100 | +++ |
| Compound of Example 9 | 300 | +++ |
| Compound of Example 11 | 100 | +++ |
| Compound of Example 12 | 200 | ++++ |
| Compound of Example 13 | 200 | ++++ |

EXAMPLE 1

A mixture of 12 g of 7-(propionamido)-2-(4-carboxyphenyl)-4H-3,1-benzoxazine-4-one, 120 ml of absolute ethanol and 9 ml of triethylamine was heated under reflux for a period of 8 hours. After being allowed to cool, the mixture was added with 9 ml of acetic acid and 500 ml of water, the precipitating crystal was filtered, and recrystallized from a solvent mixture of ethanol and water to yield 10 g of ethyl 2-(4-carboxybenzamido)-4-propionamidobenzoate having a melting point in the range of from 246° to 248° C.

Elemental Analysis

Calculated for $C_{20}H_{20}N_2O_6$: C, 62,5; H, 5.2; N, 7.3 (%); Found: C, 62.2; H, 5.5; N, 7.2 (%).

EXAMPLE 2

The procedure of Example 1 was repeated for reacting 7-(propionamido)-2-(4-carboxyphenyl)-4H-3,1-benzoxazine-4-one with n-propanol, and the reaction product was treated as in Example 1 except that the solvent for recrystallization was a mixture of dioxane and water. The product obtained was a 80% yield of propyl 2-(4-carboxybenzamido)-4-propionamidobenzoate having a melting point in the range of from 233° to 235° C.

Elemental Analysis

Calculated for $C_{21}H_{22}N_2O_6$: C, 63.3; H, 5.6; N, 7.0 (%); Found: C, 63.1; H, 5.9; N, 7.0 (%).

EXAMPLE 3

The procedure of Example 2 was repeated for reacting 7-(propionamido)-2-(4-carboxyphenyl)-4H-3,1-benzoxazine-4-one with n-butanol, and the reaction product was treated as in Example 2 to yield 75% of n-butyl 2-(4-carboxybenzamido)-4-propionamidobenzoate having a melting point in the range of from 243° to 245° C.

Elemental Analysis

Calculated for $C_{22}H_{24}N_2O_6$: C, 64.1; H, 5.9; N, 6.8 (%); Found: C, 64.0; H, 6.2; N, 6.7 (%).

EXAMPLE 4

A solution of 1.5 g of 2-(4-carboxybenzamido)-4-aminobenzoic acid in 50 ml of pyridine was mixed with 3.2 g of isobutyroyl chloride and the mixture was heated at 50° to 60° C. for a period of 2 hours. The reaction mixture was further mixed with a solution of 4 g of sodium hydroxide in 20 ml of water and concentrated under vacuum. The residue was diluted with water and hydrochloric acid was used to adjust the pH of the dilution between 1 and 2. The precipitating crystal was filtered, washed with water and recrystallized from a solvent mixture of methanol and water to thereby produce 1.1 g of 2-(4-carboxybenzamido)-4-isobutyramidobenzoic acid having a melting point in the range of from 312° to 314° C. (decompose).

Elemental Analysis

Calculated for $C_{19}H_{18}N_2O_6$: C, 61.6; H, 4.9; N, 7.6 (%); Found: C, 61.7; H, 5.1; N, 7.7 (%).

EXAMPLE 5

The procedure of Example 4 was repeated to react 2-(4-carboxybenzamido)-4-aminobenzoic acid with acetic anhydride, and the reaction product was treated as in Example 4 to yield 63% of 2-(4-carboxybenzamido)-4-acetamidobenzoic acid having a melting point in the range of from 302° to 304° C. (decompose).

Elemental Analysis

Calculated for $C_{17}H_{14}N_2O_6$: C, 59.7; H, 4.1; N, 8.2 (%); Found: C, 59.7; H, 4.2; N, 8.2 (%).

EXAMPLE 6

The procedure of Example 4 was repeated to react 2-(4-carboxybenzamido)-4-aminobenzoic acid with n-butyroyl chloride, and the reaction product was treated as in Example 4 to yield 70% of 2-(4-carboxybenzamido)-4-(n-butyramido) benzoic acid having a melting point in the range of from 297° to 299° C. (decompose).

Elemental Analysis

Calculated for $C_{19}H_{18}N_2O_6$: C, 61.6; H, 4.9; N, 7.6 (%); Found: C, 61.5; H, 5.0; N, 7.7 (%).

EXAMPLE 7

The procedure of Example 4 was repeated to react 2-(4-carboxybenzamido)-4-aminobenzoic acid with propionyl chloride, and the reaction product was treated as in Example 4 except that isopropyl alcohol was used as a solvent for recrystallization. The product obtained was a 62% yield of 2-(4-carboxybenzamido)-4-propionamidobenzoic acid having a melting point in the range of from 284° to 286° C. (decompose).

Elemental Analysis

Calculated for $C_{18}H_{16}N_2O_6$: C, 60.7; H, 4.5; N, 7.9 (%); Found: C, 60.7; H, 4.6; N, 7.8 (%).

EXAMPLE 8

The procedure of Example 4 was repeated to react 2-(4-carboxybenzamido)-4-aminobenzoic acid with isocaproyl chloride, and the reaction product was treated as in Example 4 to yield 65% of 2-(4-carboxybenzamido)-4-isocapronamidobenzoic acid having a melting point in the range of from 297° to 300° C. (decompose).

Elemental Analysis

Calculated for $C_{21}H_{22}N_2O_6$: C, 63.3; H, 5.6; N, 7.0 (%); Found: C, 63.4; H, 5.6; N, 7.0 (%).

EXAMPLE 9

A solution of 3 g of ethyl 2-(4-ethoxycarbonylbenzamido)-4-aminobenzoate in 30 ml of pyridine was mixed with 5 g of propionic anhydride, and the mixture was heated at 50° to 60° C. for a period of 2 hours. After cooling, 200 ml of water was gradually added to the reaction mixture, the precipitating crystal was filtered, and recrystallized from a solvent mixture of ethanol and water to thereby produce 2.2 g of ethyl 2-(4-ethoxycarbonylbenzamido)-4-propionamidobenzoate having a melting point in the range of from 172 to 173° C.

Elemental Analysis

Calculated for $C_{22}H_{24}N_2O_6$: C, 64.1; H, 5.9; N, 6.8 (%); Found: C, 64.3; H, 5.8; N, 6.7 (%).

EXAMPLE 10

A solution of 1.6 g of 2-(4-methoxybarbonylbenzamido)-4-aminobenzoic acid in 30 ml of pyridine was mixed with 2 g of isobutyric anhydride, and the mixture was heated at 40° to 50° C. for a period of 2 hours. Subsequently, 10 ml of water was gradually added to the reaction mixture to which was further added 10 ml of triethylamine and heated at 70° to 80° C. Upon addition of 20 ml of water, the reaction mixture was held at the reaction temperature for a period of 10 minutes, and allowed to cool. Dilute hydrochloric acid was used to adjust the pH of the reaction mixture between 2 and 3 and then the precipitating crystal was filtered, and recrystallized from a solvent mixture of methanol and water to produce 1.2 g of 2-(4-methoxycarbonylbenzamido)-4-isobutylaminobenzoic acid having a melting point in the range of from 244° to 247° C. (decompose).

Elemental Analysis

Calculated for $C_{20}H_{20}N_2O_6$: C, 62.5; H, 5.2; N, 7.3 (%); Found: C, 62.4; H, 5.4; N, 7.2 (%).

EXAMPLE 11

The procedure of Example 10 was repeated for reacting 2-(4-ethoxycarbonylbenzamido)-4-aminobenzoic acid with isobutyric anhydride, and the reaction product was treated as in Example 10 except that the solvent for recrystallization was a mixture of ethanol and water. The product obtained was a 62% yield of 2-(4-ethoxycarbonylbenzamido)-4-(isobutyramidobenzoic acid having a melting point in the range of from 230° to 235° C. (decompose).

Elemental Analysis

Calculated for $C_{21}H_{22}N_2O_6$: C, 63.3; H, 5.6; N, 7.0 (%); Found: C, 63.1; H, 5.8; N, 7.1 (%).

EXAMPLE 12

The procedure of EXample 10 was repeated for reacting 2-(4-ethoxycarbonylbenzamido)-4-aminobenzoic acid with propionic anhydride, and the reaction product was treated as in Example 10 except that acetonitrile was used as a solvent for recrystallization. The product obtained was a 60% yield of 2-(4-ethoxycarbonylbenzamido)-4-propionamidobenzoic acid having a melting point in the range of from 240° to 243° C.

Elemental Analysis

Calculated for $C_{20}H_{20}N_2O_6$: C, 62.5; H, 5.2; N, 7.3 (%); Found: C, 62.4; H, 5.4; N, 7.2 (%).

EXAMPLE 13

The procedure of Example 10 was repeated for reacting 2-(4-propoxycarbonylbenzamido)-4-aminobenzoic acid with propionic anhydride, and the reaction product was treated as in Example 10 except that ethyl acetate was used as a solvent for recrystallization. The product obtained was a 64% yield of 2-(4-propoxycarbonylbenzamido)-4-propionamidobenzoic acid having a melting point in the range of from 199° to 200° C.

Elemental Analysis

Calculated for $C_{21}H_{22}N_2O_6$: C, 63.3; H, 5.6; N, 7.0 (%); Found: C, 63.3; H, 5.8; N, 7.1 (%).

EXAMPLE 14

The procedure of Example 10 was repeated for reacting 2-(4-butoxycarbonylbenzamido)-4-aminobenzoic acid with propionic anhydride, and the reaction product was treated as in Example 10 except that the solvent for recrystallization was a mixture of water and dioxane. The product obtained was a 60% yield of 2-(4-butoxycarbonylbenzamido)-4-propionamidobenzoic acid having a melting point in the range of from 184° to 187° C.

Elemental Analysis

Calculated for $C_{22}H_{24}N_2O_6$: C, 64.1; H, 5.9; N, 6.8 (%); Found: C, 64.2; H, 6.1; N, 6.7 (%).

EXAMPLE 15

A solution of 3 g of ethyl 2-(4-carboxybenzamido)-4-aminobenzoate in 30 ml of pyridine was mixed with 3 g of propionyl chloride, and the mixture was held at 40° to 50° C. for a period of 3 hours. Subsequently, 20 ml of water was gradually added to the mixture which was held at the temperature for a period of one hour. After further addition of 100 ml of water, hydrochloric acid was used to control the pH of the reaction mixture between 1 and 2, and the precipitating crystal was filtered, washed with water, and recrystallized from a solvent mixture of ethanol and water to thereby produce 2.2 g of ethyl 2-(4-carboxybenzamido)-4-propionamidobenzoate having a melting point in the range of from 246° to 248° C.

Elemental Analysis

Calculated for $C_{20}H_{20}N_2O_6$: C, 62.5; H, 5.2; N, 7.3 (%); Found: C, 62.4; H, 5.5; N, 7.4 (%).

EXAMPLE 16

The procedure of Example 15 was repeated to react propyl 2-(4-carboxybenzamido)-4-aminobenzoate with propionic anhydride, and the reaction product was treated as in Example 15 except that the solvent for recrystallization was a mixture of dioxane and water. The product obtained was a 67% yield of propyl 2-(4-carboxybenzamido)-4-propionamidobenzoate having a melting point in the range of from 233° to 235° C.

Elemental Analysis

Calculated for $C_{21}H_{22}N_2O_6$: C, 63.3; H, 5.6; N, 7.0 (%); Found: C, 63.2; H, 5.8; N, 6.9 (%).

EXAMPLE 17

The procedure of Example 15 was repeated for reacting butyl 2-(4-carboxybenzamido)-4-aminobenzoate with propionic anhydride, and the reaction product was treated as in Example 15 to provide a 65% yield of butyl 2-(4-carboxybenzamido)-4-propionamidobenzoate having a melting point in the range of from 243° to 245° C.

Elemental Analysis

Calculated for $C_{22}H_{24}N_2O_6$: C, 64.1; H, 5.9; N, 6.8 (%); Found: C, 64.0; H, 5.9; N, 6.9 (%).

EXAMPLE 18

The procedure of Example 10 was repeated to react 2-(4-isopropyloxycarbonylbenzamido)-4-aminobenzoate with propionic anhydride, and the reaction product was treated as in Example 10 to produce a 65% yield of 2-(4-isopropyloxycarbonylbenzamido)-4-propionamidobenzoate having a melting point in the range of from 219° to 221° C.

Elemental Analysis

Calculated for $C_{21}H_{22}N_2O_6$: C, 63.3; H, 5.6; N, 7.0 (%); Found: C, 63.1; H, 5.8; N, 7.0 (%).

EXAMPLE 19

A mixture of 5 g of 7-(propionamido)-2-(4-carboxyphenyl)-4H-3,1-benzoxazine-4-one, 50 ml of dimethylformamide, 10 ml of water and 8 ml of triethylamine was heated at 80°–90° C. for a period of 10 hours. After being allowed to cool, the mixture was treated with dilute hydrochloric acid to adjust its pH between 2 and 3. The precipitating crystal was filtered, washed with water, and recrystallized from isopropyl alcohol to produce 4.1 g of 2-(4-carboxybenzamido)-4-propionamidobenzoic acid having a melting point in the range of 284° to 286° C. (decompose).

EXAMPLE 20

A mixture of 4 g of 7-(propionamido)-2-(4-ethoxycarbonylphenyl)-4H-3,1-benzoxazine-4-one, 300 ml of absolute alcohol and 10 ml of triethylamine was heated under reflux for a period of 24 hours. After the reaction, the mixture was concentrated under vacuum, and the residue was recrystallized from a solvent mixture of ethanol and water to produce 3.8 g of ethyl 2-(4-ethoxycarbonylbenzamido)-4-propionamidobenzoate having a melting point in the range of from 172° to 173° C.

EXAMPLE 21

A mixture of 3.7 g of 7-(propionamido)-2-(4-ethoxycarbonylphenyl-4H-3,1-benzoxazine-4-one, 50 ml of dimethylformamide, 3 ml of triethylamine and 0.2 ml of water was stirred at 70° to 90° C. for a period of 24 hours. After the reaction, 300 ml of water was added to the mixture, and dilute hydrochloric acid was used to control the pH of the mixture between 1 and 2. The precipitating crystal was filtered, washed with water, and recrystallized from acetonitrile to produce 3.0 g of 2-(4-ethoxycarbonylbenzamido)-4-propionamidobenzoate having a melting point in the range of from 240° to 243° C.

EXAMPLE 22

(a) Preparation of 100 mg Tablet:

A hundred grams of ground ethyl 2-(4-carboxybenzamido)-4-propionamidobenzoate was intimately blended with a mixture of 47 g of lactose, 100 g of crystalline cellulose and 3 g of magnesium stearate, and the blend was compressed into tablets each being 9 mm in diameter and 300 mg in weight.

(b) Preparation of Inhalant:

Ten grams of ground potassium salt of ethyl 2-(4-carboxybenzamido)-4-propionamidobenzoate was dissolved in distilled water. A buffer was used to control the pH of the solution at 8.5, and the solution was brought to a total volume of one liter. After being filtered through a 0.45μ membrane filter, the solution was filled into a 1-ml brown ampoul (any unfilled portions were purged with nitrogen gas), which was sterilized at 121° C. for a period of 20 minutes.

(c) Preparation of Injection:

Twenty grams of sodium salt of ethyl 2-(4-carboxybenzamido)-4-propionamidobenzoate was dissolved in distilled water for injection. Acetic acid and sodium chloride were used to control the solution to have a pH of 8.0 and an osmotic pressure of 280 mosm/kg, and the solution was brought to a total volume of one liter. After filtered through a 0.45μ membrane filter, the solution was filled into a 2-ml brown ampoule (any unfilled portions were purged with nitrogen gas) which was sterilized at 121° C. for a period of 20 minutes.

What we claim is:

1. A terephthalic acid monoamide derivative of the formula:

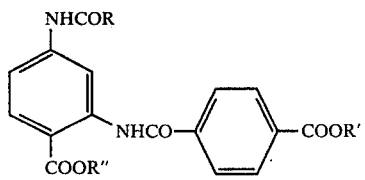

(wherein R is a straight- or branched-chain lower alkyl group; R' and R" may be the same or different, and represent a hydrogen atom, or a straight- or branched-chain lower alkyl group) or pharmaceutically acceptable salts thereof.

2. A terephthalic acid monoamide derivative of the formula:

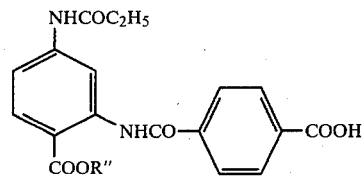

(wherein R" is a lower alkyl group) or pharmacetically acceptable salts thereof.

3. Ethyl 2-(4-carboxybenzamido)-4-propionamidobenzoate according to claim 1.

4. Propyl 2-(4-carboxybenzamido)-4-propionamidobenzoate according to claim 1.

5. n-Butyl 2-(4-carboxybenzamido)-4-propionamidobenzoate according to claim 1.

6. 2-(4-Carboxybenzamido)-4-isobutyramidobenzoic acid according to claim 1.

7. 2-(4-Carboxybenzamido)-4-acetoamidobenzoic acid according to claim 1.

8. 2-(4-Carboxybenzamido)-4-(n-butyramido)benzoic acid according to claim 1.

9. 2-(4-Carboxybenzamido)-4-propionamidobenzoic acid according to claim 1.

10. 2-(4-Carboxybenzamido)-4-isocapronamidobenzoic acid according to claim 1.

11. Ethyl 2-(4-ethoxycarbonylbenzamido)-4-propionamidobenzoate according to claim 1.

12. 2-(4-Methoxycarbonylbenzamido)-4-isobutyramidobenzoic acid according to claim 1.

13. 2-(4-Ethoxycarbonylbenzamido)-4-isobutyramidobenzoic acid according to claim 1.

14. 2-(4-Ethoxycarbonylbenzamido)-4-propionamidobenzoic acid according to claim 1.

15. 2-(4-Propoxycarbonylbenzamido)-4-propionamidobenzoic acid according to claim 1.

16. 2-(4-Butoxycarbonylbenzamido)-4-propionamidobenzoic acid according to claim 1.

17. 2-(4-Isopropyloxycarbonylbenzamido)-4-propionamidobenzoic acid according to claim 1.

18. An anti-allergic composition consisting essentially of an effective amount of a terephthalic acid monoamide derivative of the formula:

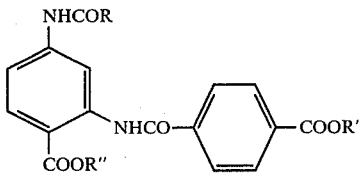

(wherein R is a straight- or branched-chain lower alkyl group; R' and R" may be the same or different, and represent a hydrogen atom or a straight- or branched-chain lower alkyl group) or a pharmaceutically acceptable salt thereof and a pharmaceutical carrier.

* * * * *